United States Patent [19]
Sander et al.

[11] Patent Number: 5,720,753
[45] Date of Patent: Feb. 24, 1998

[54] ORTHOPEDIC FASTENER

[75] Inventors: Thomas W. Sander, Winona Lake, Ind.; Daniel R. Lee, Madison; Robert B. Gangnath, Monroe, both of Conn.; David Sarver, Logansport, Ind.

[73] Assignee: United States Surgical Corporation, Norwalk, Conn.

[21] Appl. No.: 477,212

[22] Filed: Jun. 7, 1995

Related U.S. Application Data

[63] Continuation-in-part of Ser. No. 432,476, May 12, 1995, which is a continuation of Ser. No. 367,662, Jan. 3, 1995, abandoned, which is a continuation of Ser. No. 673,953, Mar. 22, 1991, abandoned, which is a continuation of Ser. No. 38,551, Mar. 26, 1993, abandoned.

[51] Int. Cl.$^6$ .................................................. A61B 17/58
[52] U.S. Cl. ............................... 606/104; 606/72; 606/73; 606/75
[58] Field of Search ............................ 606/73, 75, 232

[56] References Cited

U.S. PATENT DOCUMENTS

| | | | |
|---|---|---|---|
| 2,121,193 | 6/1938 | Hanicke | 128/92 |
| 2,381,050 | 8/1945 | Hardinge | 128/92 |
| 2,489,870 | 11/1949 | Dzus | 128/92 |
| 2,490,364 | 12/1949 | Livingston | 128/92 |
| 2,699,774 | 1/1955 | Livingston | 128/92 |
| 3,759,257 | 9/1973 | Fischer et al. | 128/92 |
| 3,760,802 | 9/1973 | Fischer et al. | 128/92 |
| 3,779,239 | 12/1973 | Fischer et al. | 128/92 |

(List continued on next page.)

FOREIGN PATENT DOCUMENTS

| | | |
|---|---|---|
| 0077868 | 10/1981 | European Pat. Off. . |
| 0230937 | 1/1987 | European Pat. Off. . |
| 0232049 | 1/1987 | European Pat. Off. . |
| 0238223 | 2/1987 | European Pat. Off. . |
| 0241240 | 4/1987 | European Pat. Off. . |
| 0409364 | 7/1990 | European Pat. Off. . |
| 0464479 | 6/1991 | European Pat. Off. . |
| 0464480 | 6/1991 | European Pat. Off. . |
| 0465910 | 6/1991 | European Pat. Off. . |
| 0739089 | 6/1932 | France . |
| 2622430 | 10/1987 | France . |
| 3445738 | 12/1984 | Germany . |
| 3509417 | 3/1985 | Germany . |
| 8633339 | 12/1986 | Germany . |
| 4106823 | 3/1991 | Germany . |
| 584855 | 8/1976 | U.S.S.R. . |
| 2084468 | 9/1981 | United Kingdom . |
| 8603666 | 12/1984 | WIPO . |
| 8910096 | 4/1988 | WIPO . |
| 8909030 | 3/1989 | WIPO . |
| 9204874 | 9/1991 | WIPO . |
| 9308747 | 10/1992 | WIPO . |

OTHER PUBLICATIONS

Anthroscopy Equipment and Supplies (Instrument Makar).
Ligament Screw System (Biomet).
The Complete Arthrex Information System (Arthrex).
Mitek GII Anchor (Mitek Surgical Products).
Mitek Anchor System (Mitek Surgical Products).
Mitek Quick Anchor (Mitek Surgical Products).
STATAK Soft Tissue Attachment Device (Zimmer).
TAG Tissue Anchor Guide System (Acufex Microsurgical Inc.).
Technique for Using the TAG Tissue Anchor—Rod Style (Acufex Microsurgical Inc.).
Technique for Using the TAG Tissue Anchor—Wedge Style (Acufex Microsurgical Inc.).
A Proposed Design For An Expanding Hip Nail (Raftopoulos).

*Primary Examiner*—Michael Buiz
*Assistant Examiner*—Daphna Shai

[57] ABSTRACT

Soft tissue is secured to bone with a surgical fastener having expandable legs. The surgical fastener is implanted into a predrilled hole in the bone and the legs are expanded by pulling a slidable pin with a flared distal end. The pin includes a breakaway notch and fins. The fastener may be fabricated from resorbable material and may be implanted arthroscopically.

16 Claims, 6 Drawing Sheets

U.S. PATENT DOCUMENTS

| | | | |
|---|---|---|---|
| 3,782,374 | 1/1974 | Fischer | 128/92 |
| 3,805,775 | 4/1974 | Fischer et al. | 128/92 |
| 3,846,846 | 11/1974 | Fischer | 3/1 |
| 3,910,281 | 10/1975 | Kletschka et al. | 128/335 |
| 4,091,806 | 5/1978 | Aginsky | 128/92 |
| 4,204,531 | 5/1980 | Aginsky | 128/92 |
| 4,227,518 | 10/1980 | Aginsky | 128/92 |
| 4,236,512 | 12/1980 | Aginsky | 128/92 |
| 4,275,717 | 6/1981 | Bolesky | 128/92 |
| 4,309,137 | 1/1982 | Tamaka et al. | 411/45 |
| 4,339,217 | 7/1982 | Lacey | 411/55 |
| 4,351,069 | 9/1982 | Ballintyn et al. | 3/1.912 |
| 4,414,967 | 11/1983 | Shapiro | 128/92 |
| 4,454,875 | 6/1984 | Pratt et al. | 128/92 |
| 4,474,517 | 10/1984 | Navoczynski | 411/45 |
| 4,519,100 | 5/1985 | Wills et al. | 3/1.9 |
| 4,519,735 | 5/1985 | Mächtle | 411/65 |
| 4,520,511 | 6/1985 | Gianezio et al. | 3/1.913 |
| 4,539,981 | 9/1985 | Tunc | 128/92 |
| 4,550,449 | 11/1985 | Tunc | 623/16 |
| 4,570,623 | 2/1986 | Ellison et al. | 128/92 |
| 4,590,928 | 5/1986 | Hunt et al. | 128/92 |
| 4,590,930 | 5/1986 | Kurth et al. | 128/92 |
| 4,632,100 | 12/1986 | Somers et al. | 128/92 |
| 4,637,765 | 1/1987 | Omata | 411/41 |
| 4,655,777 | 4/1987 | Dunn et al. | 623/16 |
| 4,656,806 | 4/1987 | Leibhard et al. | 52/704 |
| 4,669,473 | 6/1987 | Richards et al. | 128/334 |
| 4,711,232 | 12/1987 | Fischer et al. | 128/92 |
| 4,713,076 | 12/1987 | Draenert | 623/16 |
| 4,716,893 | 1/1988 | Fischer et al. | 128/92 |
| 4,738,255 | 4/1988 | Goble et al. | 128/92 |
| 4,741,330 | 5/1988 | Hayhurst | 128/92 |
| 4,760,843 | 8/1988 | Fischer et al. | 128/92 |
| 4,767,248 | 8/1988 | Pratt | 411/45 |
| 4,776,329 | 10/1988 | Trehame | 128/92 |
| 4,778,468 | 10/1988 | Hunt et al. | 623/16 |
| 4,787,378 | 11/1988 | Sodhi | 128/92 |
| 4,790,304 | 12/1988 | Rosenberg | 128/92 |
| 4,793,335 | 12/1988 | Frey et al. | 128/92 |
| 4,796,612 | 1/1989 | Reese | 128/92 |
| 4,806,053 | 2/1989 | Herb | 411/32 |
| 4,818,163 | 4/1989 | Bereiter et al. | 411/44 |
| 4,828,562 | 5/1989 | Kenna | 623/13 |
| 4,834,752 | 5/1989 | Van Kampen | 623/13 |
| 4,861,197 | 8/1989 | Calendra, Jr. | 405/259 |
| 4,870,957 | 10/1989 | Goble et al. | 128/92 |
| 4,871,289 | 10/1989 | Choiniere | 411/48 |
| 4,895,148 | 1/1990 | Bays et al. | 606/213 |
| 4,898,156 | 2/1990 | Gatturna et al. | 606/72 |
| 4,898,505 | 2/1990 | Froehlich | 411/55 |
| 4,899,743 | 2/1990 | Nicholson et al. | 606/139 |
| 4,921,383 | 5/1990 | Fischer | 411/57 |
| 4,927,421 | 5/1990 | Goble et al. | 606/73 |
| 4,946,468 | 8/1990 | Li | 606/232 |
| 4,963,144 | 10/1990 | Huene | 606/73 |
| 4,968,315 | 11/1990 | Gatturna | 606/72 |
| 4,969,892 | 11/1990 | Burton et al. | 606/218 |
| 4,976,680 | 12/1990 | Hayman et al. | 600/7 |
| 4,988,351 | 1/1991 | Paulos et al. | 606/72 |
| 5,002,550 | 3/1991 | Li | 606/139 |
| 5,013,316 | 5/1991 | Goble et al. | 606/72 |
| 5,037,422 | 8/1991 | Hayhurst et al. | 606/72 |
| 5,041,129 | 8/1991 | Hayhurst et al. | 606/232 |
| 5,046,513 | 9/1991 | Gatturna et al. | 128/898 |
| 5,053,047 | 10/1991 | Yoon | 606/223 |
| 5,076,746 | 12/1991 | Fischer et al. | 411/55 |
| 5,078,730 | 1/1992 | Li et al. | 606/228 |
| 5,080,543 | 1/1992 | Murphy | 411/60 |
| 5,084,050 | 1/1992 | Draenert | 606/77 |
| 5,085,545 | 2/1992 | Takahashi | 411/45 |
| 5,100,417 | 3/1992 | Cerier et al. | 605/139 |
| 5,102,421 | 4/1992 | Anspach, Jr. | 606/232 |
| 5,122,133 | 6/1992 | Evans | 606/73 |
| 5,156,616 | 10/1992 | Meadows et al. | 606/232 |
| 5,167,664 | 12/1992 | Hodorek | 606/73 |
| 5,167,665 | 12/1992 | McKinney | 606/75 |
| 5,176,682 | 1/1993 | Chow | 606/72 |
| 5,203,784 | 4/1993 | Ross et al. | 606/104 |
| 5,207,679 | 5/1993 | Li | 606/72 |
| 5,209,753 | 5/1993 | Biedermann et al. | 606/72 |
| 5,217,486 | 6/1993 | Rice et al. | 606/232 |
| 5,236,445 | 8/1993 | Hayhurst et al. | 606/232 |
| 5,246,441 | 9/1993 | Ross et al. | 606/53 |
| 5,258,016 | 11/1993 | DiPoto et al. | 606/232 |
| 5,268,001 | 12/1993 | Nicholson et al. | 606/72 |
| 5,336,240 | 8/1994 | Metzler et al. | 606/232 |

ORTHOPEDIC FASTENER

CROSS REFERENCE TO RELATED APPLICATIONS

This is a continuation-in-part of U.S. application Ser. No. 08/432,476, and still pending filed on May 12, 1995, which is a continuation of U.S. patent application Ser. No. 08/367,662, filed: Jan. 3, 1995 and now abandoned, which is a continuation of U.S. patent application Ser. No. 07/673,953, Filed: Mar. 22, 1991 and now abandoned, which is a continuation of U.S. patent application Ser. No. 08/038,551 filed Mar. 26, 1993, and now abandoned.

BACKGROUND

1. Field of the Disclosure

This invention relates to a surgical fastener which may be anchored into bone, and more particularly to a surgical fastener for fastening soft tissue to bone.

2. Background of the Art

Surgical bone fasteners are known in the art. Also known are devices for anchoring soft tissue, such as ligament or tendon, to bone.

Generally, these devices fall into two categories: (1) staple type systems, or (2) screw and washer type systems.

The first of these types is illustrated in U.S. Pat. Nos. 4,454,875 and 4,570,623 which show metal staples with spikes on the underside of the crosspiece to secure ligaments.

The second of these types are available as screw-washer combinations wherein the screw is fabricated from a surgically suitable metal, such as titanium, and is of self-tapping design. The washer has distal pointing spikes and a central aperture through which the screw is disposed.

Other ligament anchor systems are disclosed in U.S. Pat. Nos. 4,927,421 and 4,870,957.

The prior known devices for securing ligaments possess several disadvantages. Staples which are meant to be hammered into bone, must be made of a strong material, such as metal. This precludes the use of bioabsorbable polymers as fabrication material for the fasteners (staples). Additionally, hammering staples into the bone can be time consuming. Screw devices are also confined to metals as materials of fabrication, especially self-tapping screws. These screw devices further require a hole in the bone to be drilled which may have to be tapped, a procedure which is time consuming. Prior staples and screw ligament fasteners which are made of metal are permanently implanted into the body unless a second surgical operation is performed to remove them. In either case, implantation of metal devices does not allow for transfer of stress back to the bone/soft tissue junction as the healing proceeds. This, in turn, may slow down or impede the healing process.

Furthermore, the metal screws and staples may actually migrate from their original insertion site over a period of time. Even though healing may have occurred, a screw or staple that has backed out can be palpated and may cause pain to the patient. These screws and staples can even migrate into the joint space creating significant damage to articular cartilage and other structures.

The need therefore exists for a fastener for securing tissue to bone which will have sufficient initial anchorage strength as well as allow for gradual load sharing to provide full repair and restoration of function of the tissue and bone. The need further exists for such a device which is easily and rapidly anchored into the tissue does not harmfully migrate from its original position.

SUMMARY OF THE INVENTION

A surgical fastener for securing soft tissue, hard tissue, and/or bone plates, both absorbable and nonabsorbable, to bone is provided herein which facilitates the insertion as well as enhances healing of the tissue and bone. The surgical fastener comprises (a) a rivet having an axial bore, distal locking means for frictionally engaging the bone to secure the rivet thereto, and a proximal head portion preferably having means for holding soft tissue; and, (b) a pin receivable into said bore and proximally slidable therein, said pin having means for activating said rivet locking means in response to proximal movement of said pin within said bore. The locking means preferably includes at least two radially expandable barbed legs projecting distally from the rivet. The fastener may be fabricated from a resorbable material such as polymers of glycolide, lactide, caprolactone, polyorthoesters, polydioxanone, trimethylene carbonate, polyethylene oxide and mixtures and copolymers thereof.

The means for holding soft tissue may comprise a plurality of soft tissue engaging barbs projecting distally from the rivet head.

The means for activating the rivet locking means preferably comprises a flared portion at the distal end portion of the pin, the flared portion having a diameter greater than the diameter of the bore and being engageable with the inner surface of the rivet legs to expand the legs radially outward.

The pin may include a circumferential notch disposed between a proximal portion and a distal portion. The notch provides means for separating the proximal portion from the distal portion when a pulling force of sufficient magnitude is applied to the proximal portion. The pin may also include a plurality of ribs.

The present invention also provides a method for securing soft tissue to bone, comprising (a) drilling a hole into the bone for receiving a surgical fastener; (b) inserting the above described surgical into said hole; (c) placing the fastener so as to hold the soft tissue in contact with said bone; and (d) moving the pin proximally to activate said locking means.

The method may further include the step of applying to the proximal portion of said pin a pulling force of magnitude sufficient to break the pin at said notch.

DETAILED DESCRIPTION OF A PREFERRED EMBODIMENT

The orthopedic fastener of the present invention comprises two elements: (1) a rivet with a soft tissue-engaging barbed head and an integral sleeve possessing expandable legs, and (2) a rod-shaped setting pin terminating in a flared section and optionally possessing a circumferential groove defining a breakaway point when the retraction force applied to the pin exceeds the pin's tensile strength. When the setting pin is retracted through the sleeve of the rivet, its flared section forces the legs of the sleeve open, thereby compressing the legs against bone into which the rivet has previously been inserted, and thus anchoring the rivet firmly in place.

Figure 1:
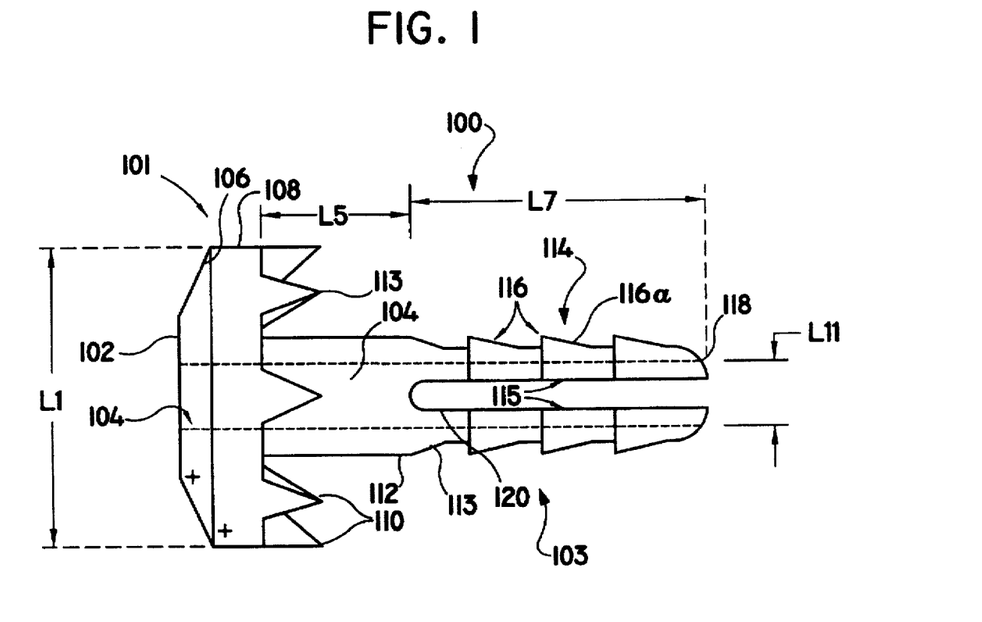
FIGS. 1, 2, and 3 illustrate, respectively, a side elevational view, a cross-sectional view, and an end view of the rivet portion of the surgical fastener of the present invention.

Referring now to FIG. 1, rivet 100 includes a head portion 101 at the proximal end and a sleeve portion 103 extending distally from head portion 101. A central (axial) bore 104 extends longitudinally through the rivet 100, i.e. through head portion 101 and sleeve portion 103, to allow for passage of pin 200 described below.

Figure 2:
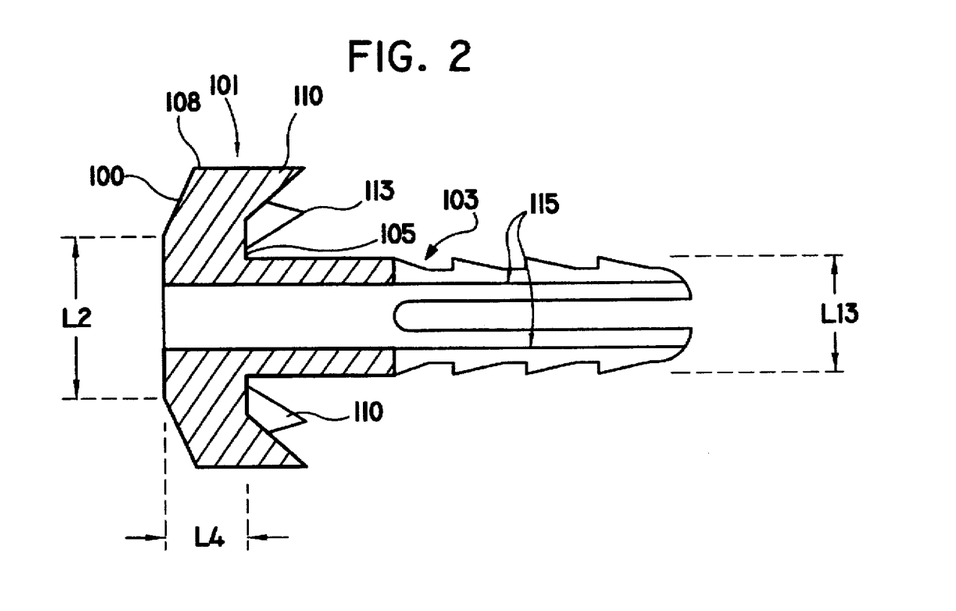
Figure 3:
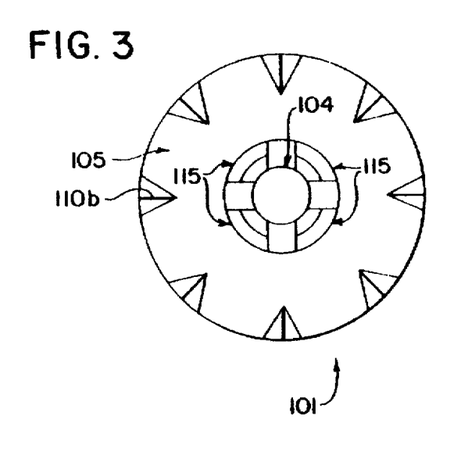

Head portion 101 includes a circular flat proximal outer surface 102 adapted to receive a suitable instrument for driving the rivet through the tissue and bone. Sloped surface 106 joins proximal outer surface 102 to peripheral cylindrical surface 108 as shown in FIGS. 1 and 2. Extending from the internal or distal surface 105 of rivet head portion 101 are a plurality of barbs 110 having pointed tips 113. As shown in FIGS. 1 and 3, the barbs 110 are spaced apart from each other and extend from the circumferential periphery of the rivet head portion 101. Alternatively, one or more of the barbs can be positioned inwardly of the circumferential portion of the head portion 101. The barbs 101 are configured and dimensioned to facilitate penetration into the tissue as well as improve anchorage of the tissue after insertion. The barbs are shown substantially triangular in shape and substantially equally spaced apart but other configurations and arrangements are contemplated which could achieve the aforementioned functions.

Sleeve portion 101 of rivet 100 has a substantially cylindrical portion 112 and a distal portion 114 having a plurality of spaced apart legs 115 which extend distally from cylindrical portion 112. Legs 115, separated by notches 120, are flexible and resilient for the reasons which will become apparent from the discussion below. Each leg 115 preferably includes a plurality of outwardly extending barbs 116 shown as substantially triangular shaped. However, other shaped barbs can clearly be utilized. Barbs 116 include an inclined distal surface 116a which is inclined at an angle from the axial orientation of the sleeve 103. Barbs 116 are configured and dimensioned to anchor the rivet 100 in the bone and to prevent the device from pulling out (i.e. proximal movement of the rivet). Sleeve 103 terminates at curved distal end 118.

In the illustrated embodiment, four spaced apart legs 115 are provided. Alternatively, a fewer or larger number of legs could be provided as long as they have sufficient flexibility and resiliency. In still another alternative embodiment, notches 120 can be eliminated so that the distal portion of sleeve 103 is tubular and composed of a suitable material that will allow expansion upon movement of the pin. In this embodiment the central bore of the head portion and proximal sleeve portion will likewise extend through the distal sleeve portion.

Figure 4:
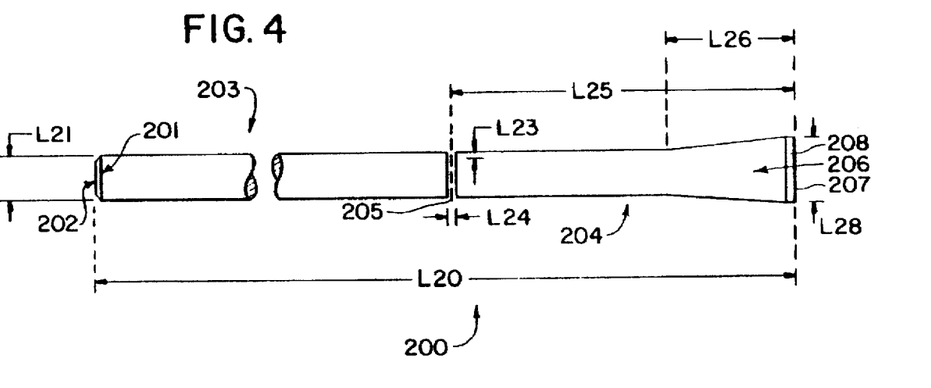
FIG. 4 illustrates an elevational view of the pin portion of the surgical fastener of the present invention.

Referring now to FIG. 4, rod-shaped setting pin comprises a shaft 200 having a proximal section 203 and a distal section 204. Proximal section has a slightly tapered proximal end 202 tapering at an angle to surface 201. Distal section 204 has a flared portion 206 extending distally outwardly and terminating in distal end surface 207. The flared portion 206 has a diameter L28 greater than the diameter of the region formed between the spaced apart legs 115 (L11 of FIG. 1), to thereby cause outward deflection of legs 115 in the manner described below.

A circumferential notch or groove 205 is formed in shaft 200 between distal section 204 and proximal section 203. The notch 205 is configured to allow breaking of the pin, i.e. separation of the distal and proximal sections 204, 203, when sufficient retraction force is applied. The notch 205 can be positioned at any desired location in shaft 200. Preferably, the notch 205 is positioned such that when the shaft 200 separates, the fracture occurs within the bore 104 of the rivet so that no portion of the shaft protrudes beyond proximal outer surface 102 of the rivet 100.

Figure 5:
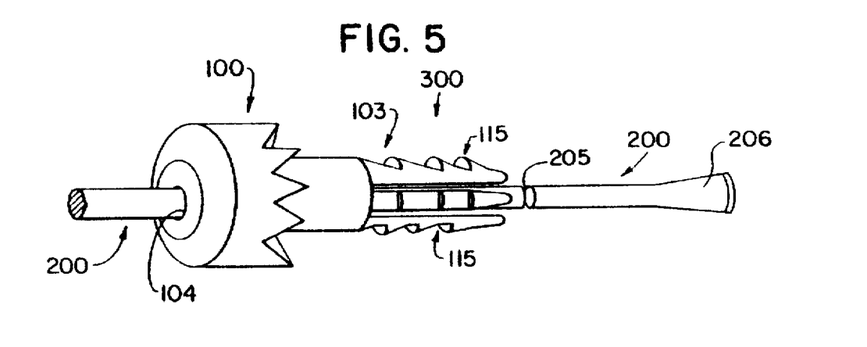
FIG. 5 illustrates a perspective view of the surgical fastener of the present invention showing the pin portion inserted through the rivet portion.

The pin 200 and rivet 100 of the present invention are assembled into orthopedic fastener 300 as shown in FIG. 5. The pin 200 is slidably disposed through axial aperture or bore 104 with flared end 206 protruding distally from the legs 115 of rivet 100.

Figure 6:
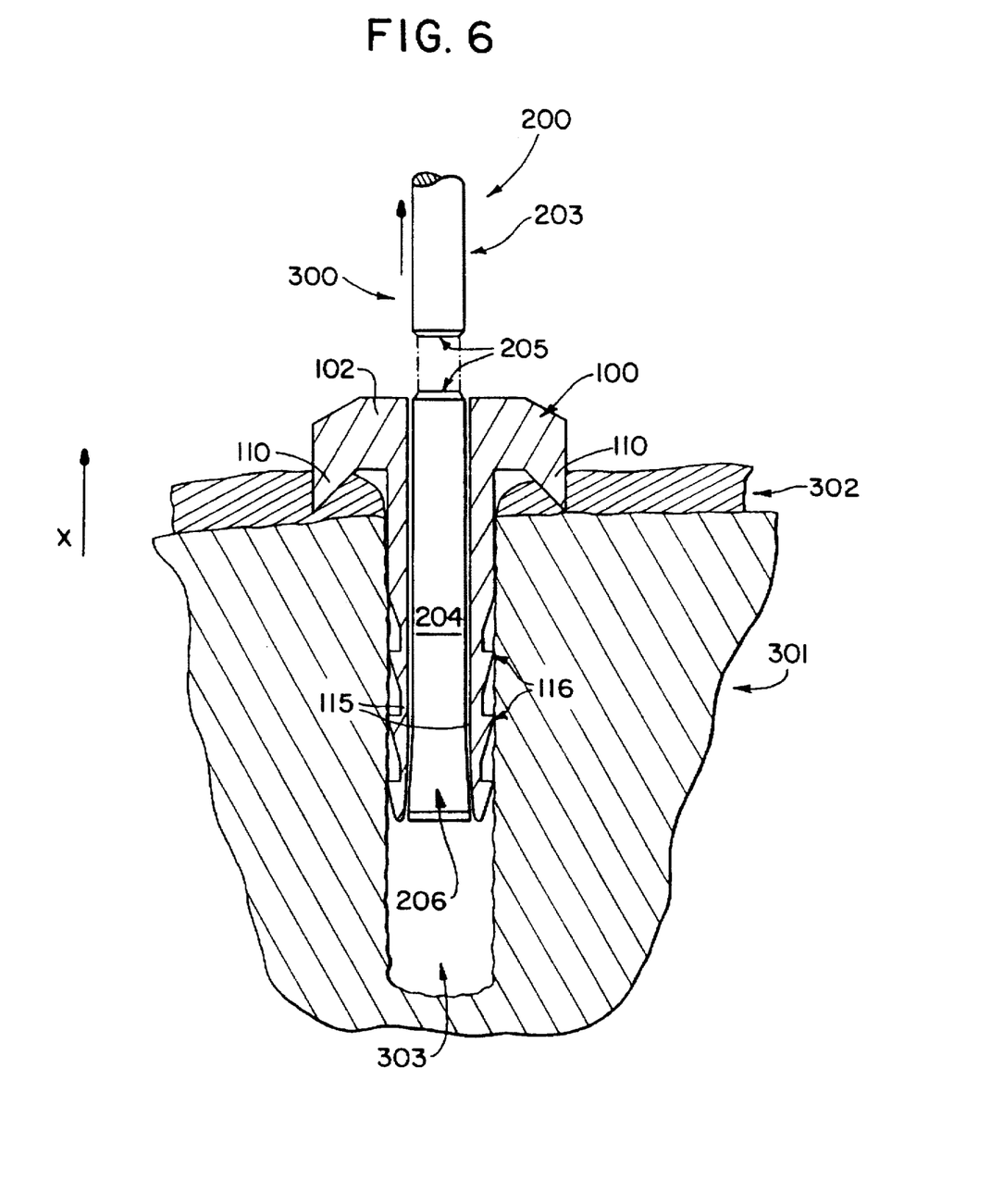
FIG. 6 illustrates the surgical fastener of the present invention implanted into bone.

To use the orthopedic fastener, a small incision or hole is made in the tissue and a hole is pre-drilled into the bone of sufficient diameter to accommodate the orthopedic fastener. Referring to FIG. 6, the orthopedic fastener 300 is inserted into the pre-drilled hole 303 in bone 301. The orthopedic fastener 300 is pressed in such that barbs 110 bite into soft tissue 302 to hold tissue 302 in close proximity to the surface of bone 301. The pin 200 is then pulled proximally by the surgeon (in the direction of arrow x) thereby urging flared section 206 through aperture 204 and between legs 115. The flared section 206 engages the inner surface of legs 115 and forces legs 115 radially outward so that barbs 116 bite into the side walls of pre-drilled hole 303 to hold the rivet firmly in place by increased friction. When the pulling force exerted by the surgeon on the proximal portion 203 of pin 200 exceeds the tensile strength of the pin, the pin 200 breaks at the notch 205 leaving a surface approximately flush with surface 102 of the rivet. The proximal portion 203 of the pin may then be discarded leaving the remainder of the orthopedic fastener in place to hold down soft tissue 302 for a time sufficient to promote healing and attachment of the soft tissue 302 to bone 301.

Figure 7A:
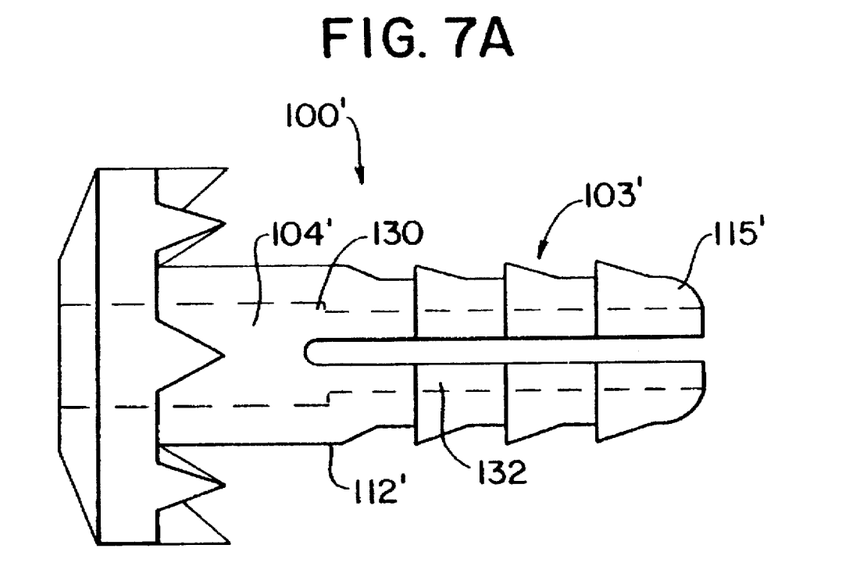
FIGS. 7A and 7B illustrate, respectively, a side elevational view and a cross-sectional view of an alternate embodiment of the rivet portion of the present invention.
Figure 7B:
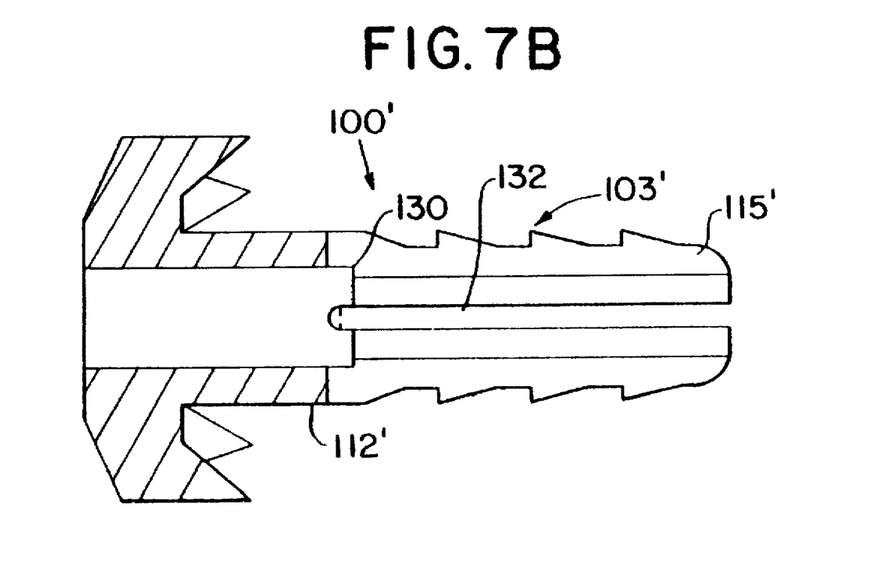
Figure 8:
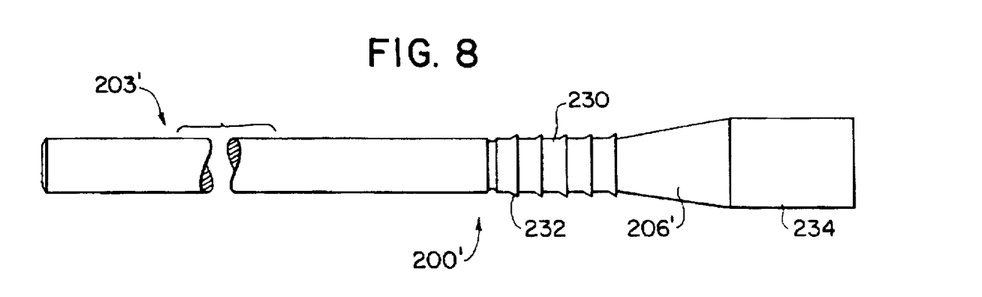
FIG. 8 illustrates an alternate embodiment of the pin portion of the present invention.

FIGS. 7A, 7B and 8, illustrate an alternate embodiment of the present invention to improve retention of the pin within the rivet. Bore 104' of rivet 100' includes a narrow portion 132 which begins at edge 130 inside cylindrical portion 112' of sleeve portion 103' and terminates at the distal portion of the legs 115'. Pin 200' has a plurality of outwardly extending ribs 230 with surfaces 232 inclined towards proximal section 203'. Ribs 230 engage edge 130 of rivet 100' to help hold pin 200' in its initial position and to prevent pin 200' from sliding distally as the pin 200' is pulled proximally in the manner described above.

Figure 10:
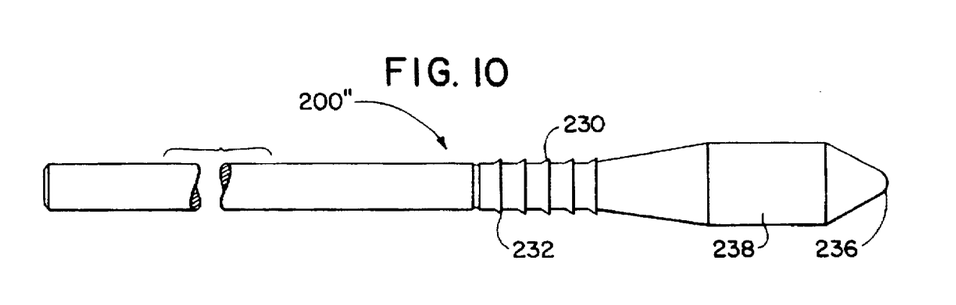
FIG. 10 illustrates an alternate embodiment of the proximal portion of the pin portion of the present invention

Pin 200 may also include a distal end portion 234 of substantially uniform, diameter disposed distally of flared section 206'. This distal end portion 234 can also be formed distally of flared section 206 of pin 200 illustrated in FIG. 4. In an alternate embodiment shown in FIG. 10, distal end portion 238 of pin 200" as a rounded conical tip 236 to facilitate entry of pin 200" into the hole in the bone.

Figure 9:
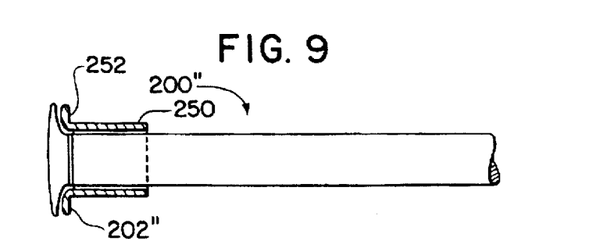
FIG. 9 illustrates an alternate embodiment of the proximal portion of the pin portion of the present invention.

To facilitate gripping the pin when pulling it proximally to spread legs 115 apart, a metal eyelet 250, having a flared portion 252 as shown in FIG. 9, may be attached to the outer surface of pin 200" directly below rim 254 formed at the proximal end 202".

Figure 11:
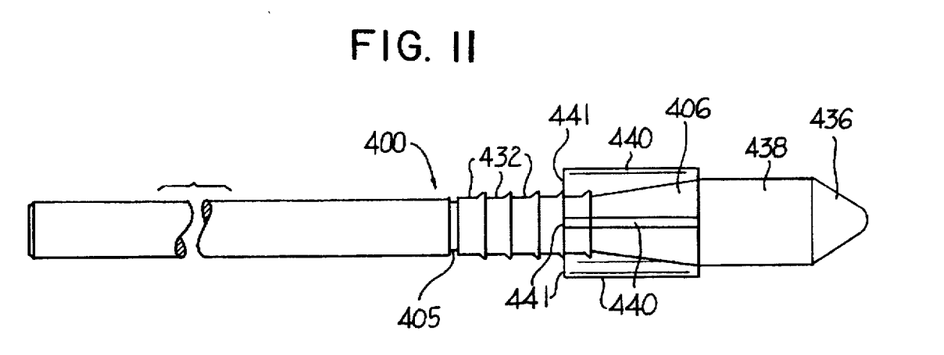
FIG. 11 is a side elevational view of an alternate embodiment of the setting pin portion.
Figure 12:
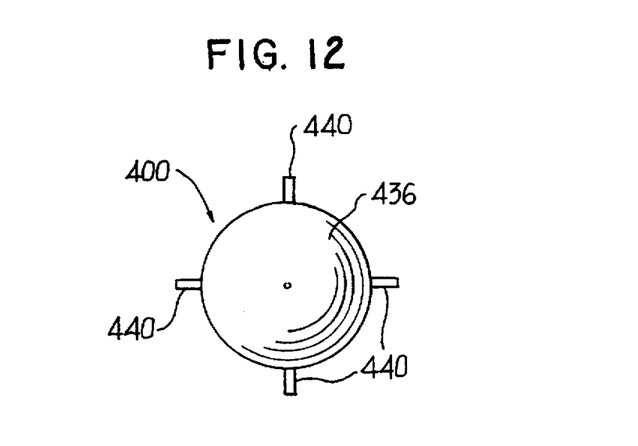
FIG. 12 is an end view of the alternative embodiment of the setting pin shown in FIG. 11.

Referring to FIGS. 11 and 12, in yet another embodiment of the orthopedic fastener, setting pin 400 is adapted for use with rivet 100 and includes outwardly extending ribs 432, breakaway notch 405, flared section 406 for camming open legs 115 of the rivet 100, and a distal end portion 438 which terminates in a rounded conical tip 436. Also included in setting pin 400 is a plurality of radially projecting fins 440 extending lengthwise along the setting pin 400 from the distal end portion 438 to the ribs 432. Use of four fins 440 is preferred although fewer or more fins may be used. The fins 440 are preferably spaced equidistantly around the setting pin 400.

Fins 440 are configured and dimensioned to respectively engage notches 120 when the setting pin 400 and rivet 100 are assembled. Thus engaged, fins 440 prevent relative rotation between the setting pin 400 and the rivet 100, thereby resisting torsional forces which may arise during the application and fixation of the orthopedic fastener.

Moreover, when the setting pin 400 is pulled to fix the orthopedic fastener 300 at an operation site, the proximal edges 441 of the fins encounter the proximal ends of the notches 120, thereby preventing further relative longitudinal movement. In this manner fins 440 facilitate the consistency and repeatability of a clean fracture along the breakaway notch 405 when the predetermined pulling force is applied to the setting pin 400, and further helps to insure that the breakage plane at breakaway notch 405 is substantially flush with the surface 102 of the rivet or positioned within axial bore 104 of the rivet at fracture.

If the orthopedic fastener is fabricated from a resorbable (bioabsorbable) material, it will stay in place in the bone for a limited period of time without the necessity for a separate surgical operation to remove it. Thereafter, the resorbable orthopedic fastener will be gradually decomposed and assimilated by the body. Examples of resorbable materials which can be utilized include homopolymers or copolymers of lactide, glycolide, polydioxonone, trimethylene. carbonate. polyorthoesters. polyethylene oxide or other bioabsorbable polymer materials or blends of these respective polymers. One preferred material is made of a copolymer of lactide and glycolide made from approximately 18% m glycolide and 82% m lactide. The rivet and setting pin may each be individually fabricated as integral or single piece structures by, for example, injection molding.

An advantageous feature of the present invention is that it is only necessary to have a pre-drilled hole in the bone, and a small incision in the surrounding tissue. The hole does not have to be tapped and the orthopedic fastener does not have to be hammered into place. Once set, the orthopedic fastener of the present invention is held in place by friction. This friction holds the fastener secure under both shear loading and pull-out force. However, this friction holding feature is not activated during insertion, which makes insertion of the fastener into the pre-drilled hole easy. Thus, the orthopedic fastener of the present invention has a friction locking feature which may be in an inactivated condition (before and during insertion of the operation site), and an activated condition (after being set by retraction of the pin 200 or 400).

The orthopedic fastener of the present invention has the further beneficial features of being more easily applied with arthroscopic procedures, for example, through a narrow cannula. The orthopedic fastener of the present invention may also advantageously be made of resorbable polymers, as stated above, thereby allowing gradual load sharing of the repaired tissue over a period of time. Resorbability also eliminates the drawbacks associated with migration of permanent, e.g. metal fasteners.

The dimensions of the rivet and pin will vary depending on its uses. Examples of some dimensions are set forth below. These dimensions provide only an example of the numerous sizes of the fasteners which can be utilized. Therefore, it should be understood that the following example of the present invention illustrates only possible dimensions of the fasteners, and the fastener of the present invention is in no way limited to these dimensions. Reference to FIGS. 1-4 will assist in understanding the dimensions set forth below.

Diameter L1 (FIG. 1) of head portion 101 of rivet 100 ranges from about 0.295 to 0.305 inches; length L5 of the cylindrical portion 112 ranges from about 0.145 to 0.155 inches; and length L7 of the distal portion 114 measures from about 0.295 to about 0.305 inches. The diameter L11 of the area between the legs 115 measures from about 0.065 to about 0.068 inches. The diameter L13 (FIG. 2) of cylindrical portion 112 ranges from about 0.113 to 0.122 inches. The width L4, of head portion 101, excluding barbs 110 is about 0.078 to 0.082 inches. The overall length L20 of pin 200 (FIG. 4) ranges from about 1.498 to 1.502 inches, with the length L25 of distal portion 204 measuring about 0.518 to 0.522 inches and length L26 of flared portion 206 measuring about 0.148 to about 0.152 inches. Diameter L28 of distal end 207 is about 0.091 inches to about 0.093 inches.

In another example, diameter L13 of cylindrical portion 112 ranges from about 0.138 to 0.142 inches, length L20 of pin 200 ranges from about 1.638 to 1.642 inches, length L25 ranges from 0.439 to 0.441 inches, and diameter L28 is about 0.109 to 0.111 inches.

It will be understood that the foregoing is only illustrative of the present invention and that various modifications can be made by those skilled in the art without departing from the scope and spirit of the present invention.

What is claimed is:

1. A surgical fastener for securing soft tissue to bone, which comprises:
   a) a rivet having an axial bore, a body portion, a head portion, and at least two expandable legs projecting from said body portion, said legs defining at least two slots therebetween; and
   b) a setting pin positioned for slidable movement within said axial bore of the rivet, said setting pin having a flared distal portion and at least one radially projecting fin configured for slidable engagement with at least one of the slots of the rivet, said setting pin being slidably movable with respect to the rivet between a first position wherein the legs of the rivet are in an unexpanded configuration and a second position wherein the legs of the rivet are expanded from the unexpanded configuration.

2. The surgical fastener of claim 1, wherein the legs of the rivet each have at least one barb for engaging bone.

3. The surgical fastener of claim 1, wherein said surgical fastener is fabricated from a bioabsorbable material.

4. The surgical fastener of claim 3, wherein said bioabsorbable material comprises a polymer selected from the group consisting of polymers of lactide, glycolide, caprolactone, polydioxanone, trimethylene carbonate, polyorthoesters, polyethylene oxide, and copolymers and blends thereof.

5. The surgical fastener of claim 1, wherein said setting pin includes a plurality of longitudinally spaced apart circumferential ribs, each of said ribs having a flat distal facing surface extending radially outward, and said rivet includes a proximally facing stop wall for engaging a respective one of the flat distal surfaces of the ribs.

6. The surgical fastener of claim 5, wherein the at least one fin extends lengthwise along the setting pin from one end thereof to said ribs.

7. The surgical fastener of claim 6, wherein the setting pin includes four fins radially positioned equidistant around the circumference thereof.

8. The surgical fastener of claim 1, wherein said head portion of said rivet includes a plurality of barbs projecting therefrom.

9. The surgical fastener of claim 1, wherein said flared distal portion of said setting pin has a diameter greater than the diameter of the axial bore of the rivet.

10. The surgical fastener of claim 1, wherein the setting pin includes a circumferential notch configured to fracture upon the application of a predetermined force to the setting pin.

11. The surgical fastener of claim 1, wherein an end portion of the setting pin terminates in a rounded conical tip.

12. A method for securing soft tissue to bone, comprising the steps of:
   a) inserting a surgical fastener into a hole in the bone, said surgical fastener including a rivet having an axial bore, a head portion and at least two expandable legs projecting from the body portion, said legs defining at least two slots therebetween and a setting pin positioned for slidable movement within the axial bore of the rivet, the setting pin having a flared portion and at least one radially projecting fin guided in one of the at least two slots and configured for slidable movement with respect to the rivet between a first position wherein the legs of the rivet are in an unexpanded configuration and a second position wherein the legs of the rivet are expanded from the unexpanded configuration; and
   b) moving the setting pin from the first position to the second position to expand said legs and moving said at least one fin into locking engagement with the hole in the bone such that said at least one fin prevents relative rotation of the rivet.

13. A surgical fastener for securing soft tissue to bone, which comprises:
   a) a rivet having an axial bore, a body portion, a head portion, and at least two radially expandable legs projecting distally from said body portion, said legs defining at least two longitudinally extending slots therebetween; and
   b) a setting pin positioned for slidable movement within said axial bore of the rivet, said setting pin having a flared distal portion and at least one longitudinally extending radially projecting fin guided in one of the at least two longitudinally extending slots and configured for slidable engagement with at least one of the slots of the rivet, said setting pin being non-rotatingly movable with respect to the rivet between a distal first position wherein the legs of the rivet are in an unexpanded configuration and a proximal second position wherein the legs of the rivet are expanded from the unexpanded configuration.

14. The surgical fastener of claim 13 wherein the flared distal portion of the setting pin includes a proximally facing inclined camming surface for expanding the legs of the rivet in response to movement of the setting pin from the distal first position to the proximal second position.

15. The surgical fastener of claim 14 wherein the setting pin includes a plurality of longitudinally spaced apart circumferential ribs, each of said ribs having a flat distal facing surface extending radially outward, and said rivet includes a proximally facing stop wall for engaging a respective one of the flat distal surfaces of the ribs.

16. The surgical fastener of claim 15 wherein said surgical fastener is made from a bioabsorbable material.

* * * * *